US010331858B2

(12) United States Patent
Miller et al.

(10) Patent No.: US 10,331,858 B2
(45) Date of Patent: Jun. 25, 2019

(54) SYSTEMS AND METHODS FOR PRESCRIPTION DRUG PACKAGING

(71) Applicant: Express Scripts, Inc., St. Louis, MO (US)

(72) Inventors: Steven B. Miller, St. Louis, MO (US); Glen D. Stettin, St. Louis, MO (US); Sharon G. Frazee, O'Fallon, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 846 days.

(21) Appl. No.: 14/505,486

(22) Filed: Oct. 2, 2014

(65) Prior Publication Data

US 2015/0128532 A1 May 14, 2015

Related U.S. Application Data

(60) Provisional application No. 61/902,007, filed on Nov. 8, 2013.

(51) Int. Cl.
*G06F 19/00* (2018.01)

(52) U.S. Cl.
CPC .................. *G06F 19/3462* (2013.01)

(58) Field of Classification Search
None
See application file for complete search history.

(56) References Cited

U.S. PATENT DOCUMENTS

| 2,970,414 A | 2/1961 | Rohdin |
| 6,411,567 B1 | 6/2002 | Niemiec et al. |
| 7,748,628 B2 | 7/2010 | Greyshock |
| 8,311,853 B1* | 11/2012 | Pankow ............. G06Q 10/00 705/2 |
| 8,392,220 B2 | 3/2013 | Knowlton et al. |

(Continued)

OTHER PUBLICATIONS

Lee, Jeannie K et al., "Effect of a Pharmacy Care Program on Medication Adherence and Persistence, Blood Pressure, and Low-Density Lipoprotein Cholesterol", Dec. 6, 2006, Journal of the American Medical Association, vol. 296, No. 21, pp. 2563-2571.*

(Continued)

*Primary Examiner* — Joy Chng
*Assistant Examiner* — Evangeline Barr
(74) *Attorney, Agent, or Firm* — Husch Blackwell LLP

(57) ABSTRACT

Systems and methods for prescription drug packaging are described. In some embodiments, a determination that a member of a pharmacy benefit plan has had a plurality of prescription drugs previously filled is made. An adjudication request for a prescription drug prescribed for the member is received. The adjudication request is based on a fulfillment request to fill the prescription drug. A determination that a blister packaging criterion has been met may be made based on a drug type of the prescription drug and a determination that the member has had the plurality of prescription drugs that have previously been filled. A blister fill instruction is transmitted based on receipt of the adjudication request and a determination that the blister packaging criterion has been met, wherein the blister fill instruction reflects that a pharmacy is to fill the prescription drug utilizing blister packaging. Additional methods and systems are disclosed.

12 Claims, 7 Drawing Sheets

(56) References Cited

U.S. PATENT DOCUMENTS

| | | | | |
|---|---|---|---|---|
| 2005/0209879 A1* | 9/2005 | Chalmers | ............... | G06Q 50/22 |
| | | | | 705/2 |
| 2008/0281630 A1* | 11/2008 | Sekura | ................... | A61B 5/411 |
| | | | | 705/2 |
| 2009/0198517 A1* | 8/2009 | Ruben | ................... | G06Q 10/087 |
| | | | | 705/3 |
| 2013/0340390 A1* | 12/2013 | Carson | ................... | B25J 9/0096 |
| | | | | 53/411 |

OTHER PUBLICATIONS

"Interventions to increase adherence to prescribed medicine", Jan. 2009, National Collaborating Centre for Primary Care (UK), London: Royal College of General Practitioners (UK), NICE Clinical Guidelines, No. 76.*

Beena Jimmy, Jimmy Jose; "Patient Medication Adherence: Measures in Daily Practice"; Apr. 9, 2011; Oman Medical Journal; vol. 26, No. 3: 155-159.*

* cited by examiner

SYSTEMS AND METHODS FOR PRESCRIPTION DRUG PACKAGING

CROSS-REFERENCE TO A RELATED APPLICATION

This application claims the benefit of U.S. provisional patent application 61/902,007 filed on 8 Nov. 2013, entitled "Systems and Methods for Packaging Selection," the entire disclosure of which is incorporated herein by reference.

FIELD

The field relates to prescription drug packaging, and more particularly to methods and systems for prescription drug packaging.

BACKGROUND

Prescription medications, if taken as prescribed, may have a positive impact to a person's health. Nevertheless, patients of a pharmacy often do not take their prescription drugs properly. Indeed, consistently taking medications on schedule may prove difficult to the patient. Whether it is from forgetfulness, inconvenience, or discomfort, doses are often missed. In addition, patients often do not timely renew or refill their prescription, or may even quit taking the prescribed medication altogether. Some patients may intend to continue taking the prescribed medication but wait too long to reorder additional prescription drugs. In other words, patients may miss doses because they are waiting for the renewal or refill of a prescription to be filled. Additionally, for a renewal, the pharmacy generally requires a new written prescription from the patient's doctor approving the continuation of therapy. In this case, it is likely that the doctor would request an office visit before writing the prescription. Scheduling conflicts and overall delays due to the required visit can result in prolonged nonadherence to the drug regimen. The patient's health and well-being may be adversely affected.

DETAILED DESCRIPTION

Figure 1:
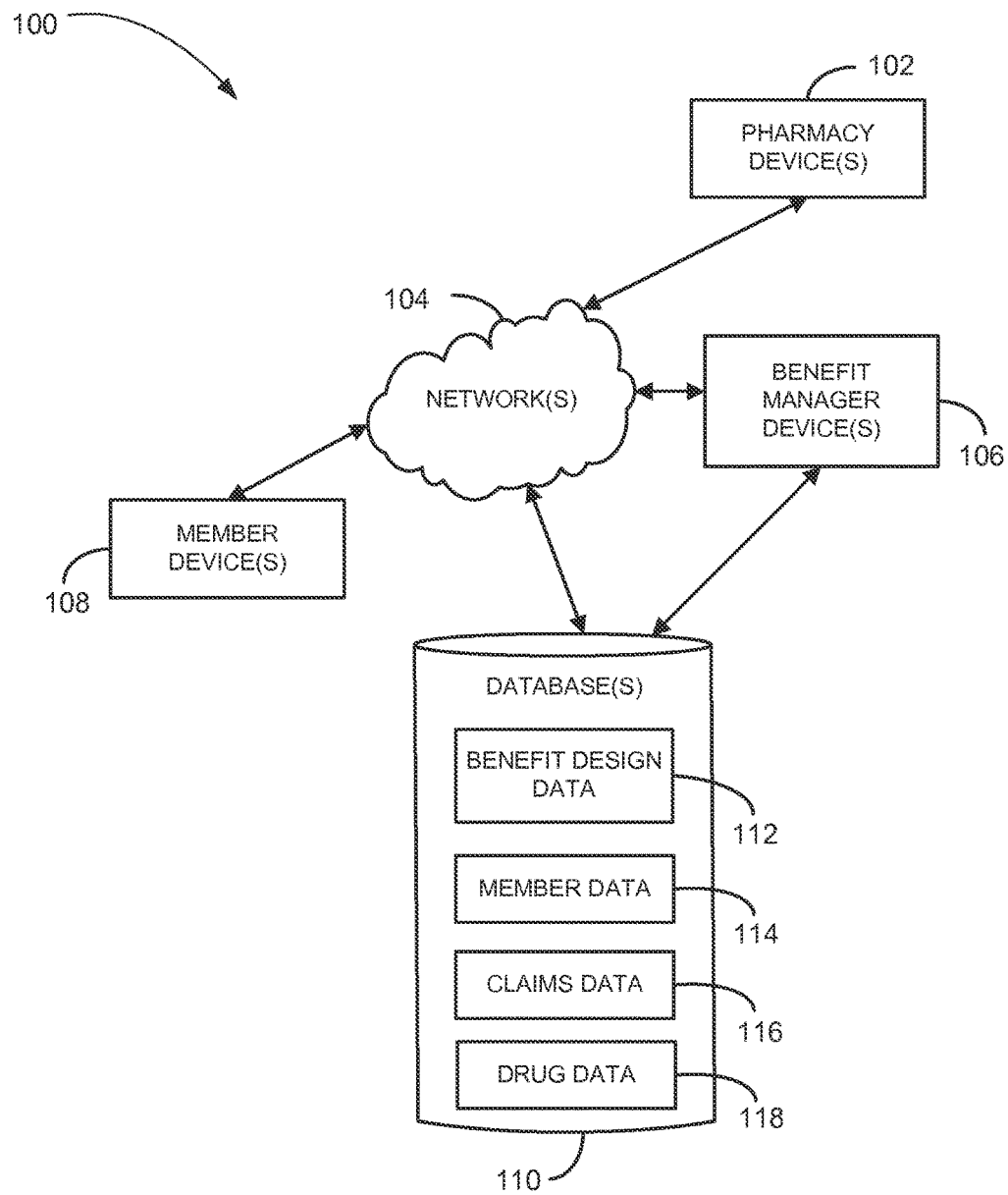
FIG. 1 is a block diagram of an example system according to an example embodiment.

Example systems and methods for prescription drug packaging are described. In the following description, for purposes of explanation, numerous specific details are set forth in order to provide a thorough understanding of example embodiments. It will be evident, however, to one of ordinary skill in the art that embodiments of the invention may be practiced without these specific details.

In general, a client engages a pharmacy benefit manager (PBM) to offer a drug benefit program. Examples of clients include governmental organizations (e.g., federal government agencies, the Department of Defense, the Centers for Medicare and Medicaid Services and state government agencies), middle market companies, large national employers, health insurance companies that have carved out the drug benefit, and the like. A person who is a participant or member of a drug benefit program offered by the client may obtain prescription drugs according to pricing, pharmacy selection, rebates, discounts, and the like provided by the terms of the drug benefit program.

The client's offered drug benefit program may be a stand-alone drug benefit operated by the PBM, or as part of a health care benefit operated by a health insurance company where the PBM services are offered directly by the health insurance company or offered indirectly by the PBM on behalf of the health insurance company. The drug benefit program may also be offered as part of the health care benefit provided through a public or private health care exchange.

Some of the operations of the PBM may include the following. A member or a person acting on behalf of the member attempts to obtain a prescription drug at a retail pharmacy location of a pharmacy where the member can obtain drugs in a physical store from a pharmacist or pharmacist technician. The pharmacy can be associated with a single retail pharmacy location, or can be a pharmacy chain that includes multiple retail pharmacy locations. The pharmacy then submits a claim to the PBM for the prescription drug. The PBM performs certain adjudication operations including verifying the eligibility of the member, reviewing the formulary to determine appropriate co-pay, coinsurance, and deductible for the prescription drug, and performing a drug utilization review (DUR) on the member. The PBM then provides a response to the pharmacy following performance of the aforementioned operations. The aforementioned adjudication operations generally occur before the co-pay is received and the prescription drug dispensed. However, the operations may occur simultaneously, substantially simultaneously, or in a different order. In addition, more or less adjudication functions may be performed as part of the adjudication process.

As part of the adjudication, the client (or typically the PBM on behalf of the client) ultimately reimburses the pharmacy for filling the prescription drug when the prescription drug was successfully adjudicated. The amount of reimbursement paid to the pharmacy by the client and/or PBM may be based at least in part on the type of pharmacy network in which the pharmacy is included. Other factors may be used to determine the reimbursement amount in addition to the type of pharmacy network. In an embodiment in which the PBM reimburses the pharmacy on behalf of the client, the PBM may subsequently bill the client for the amount of the reimbursement, and typically also for the services of the PBM in adjudicating the claim and otherwise managing the drug benefit program. The amount that the client is billed by the PBM may be based at least in part on the reimbursement paid to the pharmacy and the type of pharmacy network in which the pharmacy is included. Other factors may be used to determine the billed amount.

The PBM may offer mail order drugs as part of its services, or a third party may offer mail order drugs to members of the PBM. The PBM may adjudicate the pharmacy claim for the mail order prescription drugs in the same or a similar manner to the process described above.

As part of the services that the PBM offers to the client, the services offered through a mail order pharmacy and/or retail pharmacy, or otherwise to the member, the PBM may seek to reduce the cost to the client for the prescription drugs taken by its members and/or to improve the adherence of the members of a prescription drug regimen.

The PBM, the mail order pharmacy, and/or the retail pharmacy may have prescription drugs fulfilled with blister packaging instead of other types of packaging (e.g., prescription drug bottles). In some embodiments, filling one prescription drug, or some of the prescription drugs, of the member fulfilled with blister packaging and the remaining prescription drugs of the patient with standard packaging may increase the adherence of the patient with the prescription drugs included in the standard packaging, the blister packaging, or both.

FIG. 1 is a block diagram of an example system 100, according to an example embodiment. The system 100 is an example embodiment in which prescription drug packaging may be performed. The system 100 includes a pharmacy device 102 in communication with a benefit manager device 106 over a network 104. The system may also include a member device 108.

The pharmacy device 102 may include pharmacy hardware and/or software of to enable the pharmacy (e.g., a mail order pharmacy and/or or a retail pharmacy) to fulfill prescription drug orders. The pharmacy device 102 may be operated in an automated manner as directed by an operator (e.g., a pharmacist or pharmacist technician), manually (e.g., by a pharmacist or pharmacist technician), or otherwise. Examples of pharmacy operations that may be performed by pharmacy device 102 include filling a prescription after removing pharmaceuticals from inventory, labeling a container with prescription information, filling a container, blister pack, or other packaging with the pharmaceutical, verifying the type and quantity of the pharmaceutical in the container with that which is printed on the label, capping or otherwise closing the packaging, preparing the packaging for shipment or other delivery to a patient associated with the prescription, and the like.

In some embodiments, the pharmacy device 102 may be a device associated with a retail pharmacy location (e.g., an independent pharmacy or a pharmacy location of a local or national chain such as WALGREENS, DUANE REED or CVS), a grocery store with a retail pharmacy (e.g., an independent grocery store or a grocery store location of a local or national chain such as ALDI, KROGERS, or SCHNUCKS) or a general sales store with a retail pharmacy (e.g., an independent general sales store or a store location of a local or national chain such as WALMART or TARGET) or other type of pharmacy location at which a member attempts to obtain a prescription. In some embodiments, the pharmacy device 102 may be utilized to submit the claim to the PBM for adjudication. Additionally, in some embodiments, the pharmacy device 102 may enable information exchange between the pharmacy and the PBM, for example, to allow the sharing of member information such as drug history, and the like, that may allow the pharmacy to better service a member (e.g., by providing more informed therapy consultation and drug interaction information).

In some embodiments, the pharmacy device 102 may be associated with a mail order pharmacy. The mail order pharmacy may fill or refill the prescription, and may deliver the prescription drug to the member via a parcel service in accordance with an anticipated need, such as a time-wise schedule, or the like. As such, the member may not need to visit the retail pharmacy store in person to have the prescription refilled and/or to pick up the refilled prescription. In addition to the convenience of receiving the refills of the prescription directly to the member's home or other designated location of delivery, the cost of the prescription drugs purchased through a mail order delivery pharmacy may be less than the cost of the same prescription drugs purchased from a retail pharmacy. The lower costs available through the mail order pharmacy may be the result, for example, of economies available to the mail order pharmacy that may be at least partially passed along to the member as well as the savings realized by the client. The lower costs available through the mail order pharmacy may be the result of a lower co-pay required by the member according to a health care plan, under which the member may receive the prescription drugs. The pharmacy device 102 may communicate with the benefit manager device 106 in a similar manner as described above.

Examples of the devices 102, 106, 108 include a set-top box (STB), a receiver card, a mobile telephone, a personal digital assistant (PDA), a display device, a portable gaming unit, and a computing system; however other devices may also be used. For example, the devices 102, 106, 108 may include a mobile electronic device, such an IPHONE or IPAD device by Apple, Inc., mobile electronic devices powered by ANDROID by Google, Inc., and a BLACKBERRY device by Research In Motion Limited. The devices 102, 106, 108 may also include other computing devices, such as desktop computing devices, notebook computing devices, netbook computing devices, gaming devices, and the like. Other types of electronic devices may also be used.

The network 104 by which one or more than one of the devices 102, 106, 108 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may also include optical communications. Other conventional and/or later developed wired and wireless networks may also be used. In some embodiments, the network 104 may include proprietary network communication technologies such as secure socket layers (SSL) technology, technology found in a prescribing network (e.g., the electronic prescribing network operated by Surescripts of Arlington, Va.), and the like.

The benefit manager device 106 is a device operated by an entity at least partially responsible for the management of a drug benefit program. While the entity operating the benefit manager device 106 is typically a PBM, other entities may operate the benefit manager device 106 either on behalf of themselves, the PBM, or another entity. In some embodiments, the benefit manager that provides the drug benefit may also provide one or more than one additional benefits including a health benefit, a dental benefit, a vision benefit, a wellness benefit, a radiology benefit, a pet care benefit, an insurance benefit, a long term care benefit, a nursing home benefit, and the like.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending account (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication operations including verifying the eligibility of the member, reviewing the formulary to determine appropriate co-pay, coinsurance, and deductible for the prescription drug, and performing a DUR on the member. The PBM then provides a response to the pharmacy following performance of the aforementioned operations. As part of the adjudication, the client (or the PBM on behalf of the client) ultimately reimburses the pharmacy for filling the prescription drug when the prescription drug was successfully adjudicated. The aforementioned adjudication operations generally occur before the co-pay is received and the prescription drug dispensed. However, the operations may occur simultaneously, substantially simultaneously, or in a different order. In addition, more or less adjudication operations may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network. For example, if the member pays the pharmacy for the prescription without using the prescription drug benefit provided by the benefit manager, the amount of money paid by the member may be higher and the amount of money received by the pharmacy for dispensing the prescription drug and for the prescription drug itself may be higher.

In some embodiments, the pharmacy device 102 and/or the benefit manager device 106 are operated by a single entity. In other embodiments, the pharmacy device 102 and/or the benefit manager device 106 are operated by different entities. In some embodiments, the pharmacy device 102 and/or the benefit manager device 106 are jointly operated (e.g., on a single device or on a pool of devices), while in other embodiments, pharmacy device 102 and the benefit manager device 106 are operated separately.

The member device 108 is used by a device operator. The device operator may be a member of a drug benefit program, a patient of a pharmacy, or the like. However, the device operator may be another person operating the member device 108 on behalf of the member. Examples of such people include parents, guardians and caregivers. Accordingly, while some illustrative embodiments may be described herein in which the device operator may be the member, the device operator may be an individual other than the member. In some embodiments, the device operator may be a patient of a pharmacy who is not a member of PBM. While the member is generally described herein as being the device operator, generally any of the aforementioned persons may be substituted for the member.

In some embodiments, the member may utilize the member device 108 to communicate with the benefit manager (e.g., through the benefit manager device 106) or a pharmacy (e.g., through the pharmacy device 102).

By way of example, the member device 106 may communicate with the benefit manager device 106 to enable a member to have a prescription filled through a pharmaceutical delivery channel (e.g., at a retail pharmacy or via a mail order pharmacy). The member operating the member device 106 may be a person who has one or more than one prescription drugs prescribed to the person by a medical healthcare professional.

The member device 106 may be associated with a single member, or with multiple members. A member may use a single member device or multiple member devices. In some embodiments, a communication may be made to the member directly through the member device 106. For example, the member may get blocked at a retail pharmacy location from receiving a prescription drug under the drug benefit program associated with the member and then receive the notification through the member device 106, from the pharmacist, or both regarding the blockage. The member may also receive a letter in the mail or by an e-mail explaining the blockage.

The pharmacy device 102 and/or the benefit manager device 106 may be in communication directly (e.g., through local storage) and/or through the network 104 (e.g., in a cloud configuration or software-as-a-service) with a device that stores a database 110. The database 110 may be deployed on the benefit manager device 106, the pharmacy device 102, both the benefit manager device 106 and the pharmacy device 102, partially on the benefit manager device 106 and the pharmacy device 102, on a separate device, or may otherwise be deployed. The database 110 may store benefit design data 112, member data 114, claims data 116, and drug data 118. The system 100 may include a single database 110, or multiple databases 110, maintained by respective devices operated by or on behalf one or a number of different persons and/or organizations.

The benefit design data 112 may include member benefits provided under a drug benefit program, the presence and/or status of a fill criterion for a prescription drug (e.g., including a blister packaging criterion) and of a preferred pharmaceutical delivery channel, one or more than one preferred pharmaceutical delivery channels associated with a member, one or more than one exemptions associated with a member, and the like.

The benefit design data 112 may also include formulary data reflecting what drugs are on and off the formulary, co-pay data including the amount of co-pays for certain tiers of drugs, clinical/disease management, data regarding programs selected for member populations of clients, pharmacy network data reflecting the pharmacies that are in a particular pharmacy network, or the like. The benefit design data 112 may be at the member level, the client level, or otherwise. Benefit design data for other benefits beyond prescription drug benefits may be stored as the benefit design data 112.

The member data 114 includes information regarding the members associated with the benefit manager. Examples of the member data 114 include name, address, telephone number, e-mail address, prescription drug history, and the like. The member data 114 may include a plan sponsor identifier that identifies the plan sponsor associated with the member and/or a member identifier that identifies the member to the plan sponsor. The member data 114 may include a member identifier that identifies the plan sponsor associated with the patient and/or a patient identifier that identifies the patient to the plan sponsor. The member data 114 may also include, by way of example, dispensation preferences such as type of label, type of cap, message preferences, language preferences, or the like. The member data 114 may be accessed by various devices in the pharmacy to obtain information utilized for fulfillment and shipping of prescription orders.

In some embodiments, the member data 114 may include information for persons who are patients of the pharmacy but are not members in a benefit plan being provided by the benefit manager. For example, these patients may obtain drug directly from the pharmacy, through a private label service offered by the pharmacy, or otherwise. In general, the use of the terms member and patient may be used interchangeably herein.

The claims data 116 may include medical, dental, vision, and/or prescription drug claims made by or on behalf of the member. In some embodiments, the claims data 116 may include prescription drug claims that have been adjudicated for each member of a drug benefit program (e.g., prescribed drugs, prescription history, pharmacy usage, co-pay information, and the like).

The claims data 116 includes information regarding pharmacy claims adjudicated by the PBM under a drug benefit program provided by the PBM for one, or more than one, client. In general, the claims data 116 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility. Additional information may be included in the various claims of the claims data 116.

In some embodiments, other types of claims may be stored in the claims data 116. For example, medical claims, dental claims, wellness claims, or other type of health care-related claims for members may be stored as a portion of the claims data 116.

The drug data 118 may include drug name (e.g., technical name and/or common name), other names by which the drug is known by, active ingredients, an image of the drug (e.g., in pill form), and the like. The drug data 118 may include a dosage format (e.g., pill, spray, liquid, etc.) and/or the packaging formats (e.g., filled bottle, filled blister packaging, pre-filled unit of use packaging, etc), that are available to or for the drug. The drug data 118 may include information associated with a single medication or multiple medications.

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be a different device type. Moreover, system 100 shows a single network 104, however, multiple networks can be used. The multiple networks may communicate in series with each other to link the devices 102, 106, 108 or in parallel to link the devices 102, 106, 108. In some embodiments, the devices 102, 106, 108 may be in a client-server relationship with one another, a peer-to-peer relationship with one another, and/or in a different type of relationship with one another.

Figure 2:
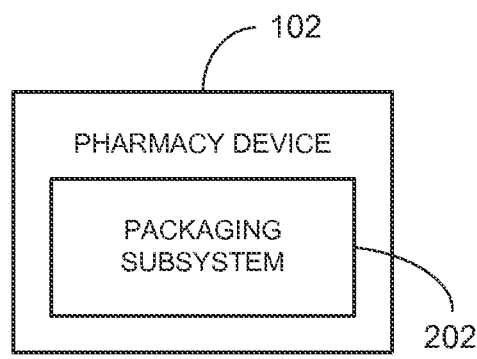
FIG. 2 is a block diagram of an example pharmacy device that may be deployed within the system of FIG. 1, according to an example embodiment.

FIG. 2 illustrates the pharmacy device 102, according to an example embodiment. The pharmacy device 102 may include a packaging subsystem 202. The packaging subsystem 202 may enable prescription drug packaging. The pharmacy device 102 may be deployed in the system 100, or may otherwise be used.

Figure 3:
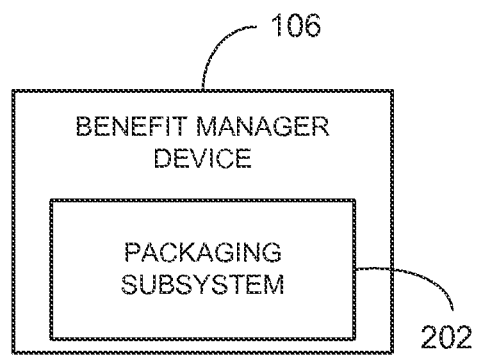
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may include the packaging subsystem 202. The packaging subsystem 202 may enable prescription drug packaging. The benefit manager device 106 may be deployed in the system 100, or may otherwise be used.

Figure 4:
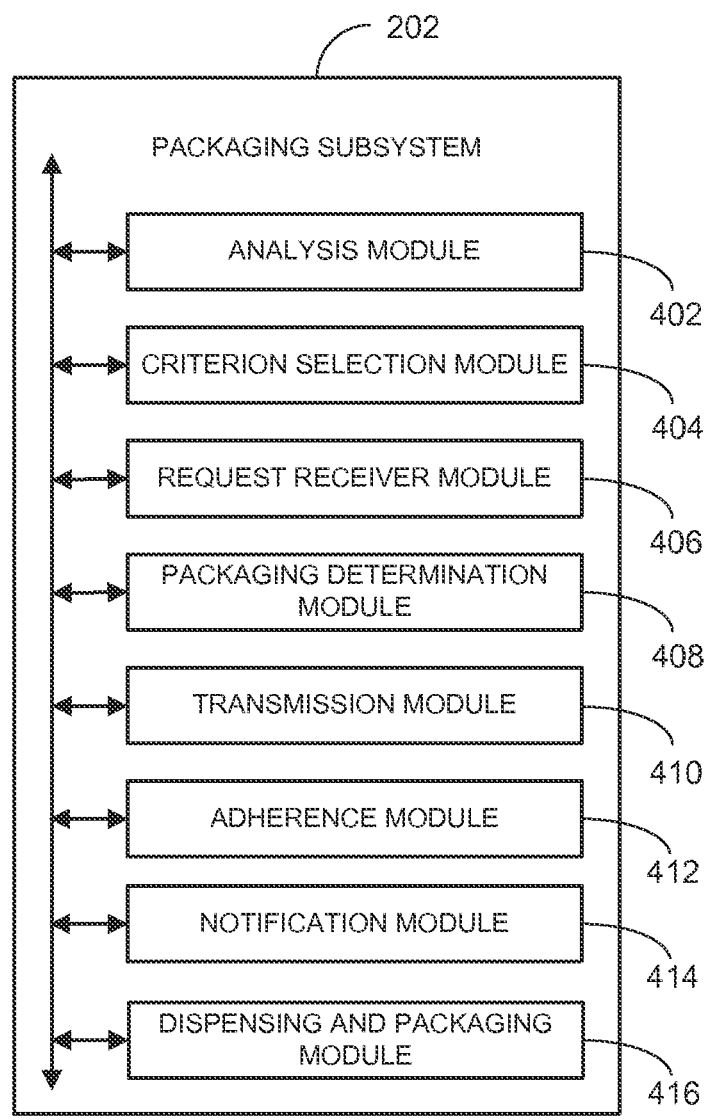
FIG. 4 is a block diagram of an example packaging subsystem that may be deployed within the pharmacy device of FIG. 2 or the benefit manager device of FIG. 3, according to an example embodiment.

FIG. 4 illustrates an example packaging subsystem 202 that may be deployed in the pharmacy device 102, the benefit manager device 106, or otherwise deployed in another system. One or more modules are communicatively coupled and included in the packaging subsystem 202 to package prescription drugs. The modules of the packaging subsystem 202 that may be included are an analysis module 402, a criterion selection module 404, a request receiver module 406, a packaging determination module 408, a transmission module 410, an adherence module 412, a notification module 414, and a dispensing and packaging module 416. Other modules may also be included.

In some embodiments, the modules of the packaging subsystem 202 may be distributed so that some of the modules are deployed in the pharmacy device 102 and some modules are deployed in the benefit manager device 106. In one embodiment, the modules are deployed in memory and executed by a processor coupled to the memory. The functionality contained within the modules 402-416 may be combined into a lesser number of modules, further divided among a greater number of modules, or redistributed among existing modules. Other configurations including the functionality of the modules 402-416 may be used.

In some embodiments, the analysis module 402 analyzes prescription drugs that have been prescribed to a patient population and/or taken by the patient population and identifies one, or more than one, prescription drugs among the prescribed and/or taken prescription drugs as being a maintenance drug that could be fulfilled through prescription bottle fulfillment or blister packaging fulfillment. The patient population may include all members of a single client, a subset of all members of a single client, all or a subset of members of multiple clients, or the like. For example, certain types of drugs may be commonly taken by the population and are in the form of a pill or other type of drug that could be packaged in at least blister packaging.

Data reflecting the prescription drugs prescribed to the patient population may come from data received from prescribers, from an electronic prescribing network (e.g., directly from the network or through a device associated with an entity responsible for electronic prescribing network), PBMs, or otherwise. Data reflecting the prescription drugs taken by the patient population may come from the claims data 116, claims data received from another source, or otherwise.

The analysis module 402 may thereby identify one, or more than one, type of drugs for the patient population as being candidates for selection by the criterion selection module 404. For example, a prescription drug that is taken through an inhaler may be identified as not being a candidate for selection because of unavailability through prescription bottle fulfillment or blister packaging fulfillment (e.g., but rather as being available for unit-of-use fulfillment), while a prescription drug taken in tablet form may be identified as being a candidate for selection as being available through prescription bottle fulfillment or blister packaging fulfillment.

In some embodiments, the analysis module 402 uses the drug data 118 (as stored in the database 110 and/or in another database) in identifying candidate drugs for selection. For example, the drug data 118 may include packaging information regarding the prescription drugs. In some embodiments, the pharmacy device 102 analyzes or accesses its drug inventory including, in some embodiments, packaging information to identify candidate drugs for selection.

The analysis of the prescription drugs to identify prescription drugs as being a maintenance drug may be made by the analysis module 402 in a number of different methods. In some embodiments, a prescription drug is identified as a maintenance drug (or as commonly used as a maintenance drug) in the drug data 118. Such identification may be made by the manufacturer of the prescription drug, a health care provider associated with the prescription drug, a PBM or other benefit manager associated with the prescription drug, a governmental organization, or a different entity.

In some embodiments, a PBM may analyze the claim data 116 of one or a number of members to identify prescription drugs as maintenance drugs. For example, claims that reflect continuing usage by members over a period of time (e.g., multiple refills) may be identified as maintenance drugs, while claims that reflect acute usage by members (e.g., one-time usage during a certain time period) may be identified as not being a maintenance drug.

The criterion selection module 404 selects the blister packaging criterion used for some or all of the drugs (e.g., in one class, or more than one class of drugs) based on analysis performed by the analysis module 402. In general, the blister packaging criterion establishes one, or more than, criterion for determining whether a prescription drug should be filled with blister packaging instead of other packaging that may be available (e.g., a prescription bottle of a particular size). The blister packaging criterion may be made in general for a type of prescription drug across an entire patient population, or may be specific to certain patients or groups of patients.

In some embodiments, blister packaging includes a cavity or pocket made from a formable web, usually a thermoformed plastic. In some embodiments, blister packaging includes a backing of paperboard or a lidding seal of aluminum foil or plastic. Non-blister packaging generally includes other types of prescription drug containers such as bottles in a variety of sizes that are sealed with lids. The type and/or characteristics of packaging available may depend on the pharmacy devices 102 available in the system 100.

In some embodiments, the analysis module 402 reviews a number of commonly used maintenance drugs by the patient population. The number may be a threshold, may be a number designated by a person or entity associated with the creation, deployment, and/or usage of the packaging determination subsystem 200. By way of example, the number and type of drugs may be such as to enable a certain percentage usage across the patient population of blister packaging on at least one prescription drug that is likely to be taken by a member in the patient population. In some embodiments, not all prescription drugs taken by a patient or member are ultimately selected for blister packaging. Rather, a subset of prescription drugs are selected while member adherence improves for all prescription drugs (including those not in blister packaging).

In some embodiments, the analysis module 402 utilizes one, or more than one, models and/or classifiers for use in analysis and/or identification of prescription drugs as being a common maintenance drug. The analysis module 402 may include models and/or classifiers such as group method of data handling, naive bayes, k-nearest neighbor algorithm, majority classifier, support vector machine, logistic regression, uplift modeling, or the like. Such functionality may enable a more sophisticated selection of prescription drugs to be packaged in blister packaging, and/or may further individualize the selection of one, or more than one, prescription drug to be packaged in blister packaging for a particular patient.

The analysis module 402 determines that a person (e.g., a member of a pharmacy benefit plan and/or a patient of a pharmacy) has had prescription drugs that have previously been filled. The drugs may have been filled through an entity making the determination through the analysis module 402, or through another entity (e.g., by a retail pharmacy or a mail order pharmacy). The determination relative to the member may be made through analysis of the claims data 116 associated with the member or otherwise.

In some embodiments, the adherence module 412 may determine the adherence of the member. When the member's adherence is below a certain threshold, the analysis performed by the analysis module 402 may be made to determine whether the member is an appropriate candidate to receive (or continue to receive) blister packaging for one, or more than one, type of prescription drug. When the member's adherence is above a certain threshold, the member may not be a candidate to receive blister packaging (e.g., for adherence reasons) based on the analysis performed by the analysis module 402.

The request receiver module 406 receives a request for a prescription drug prescribed to the member. In some embodiments, the request is an adjudication request associated with a fulfillment request to fill the prescription drug. In general, the adjudication request reflects that the member is seeking to have a prescription drug filled as either a new prescription or renewal. In some embodiments, the request is a fulfillment request to fill the prescription drug on behalf of the patient.

The packaging determination module 408 determines packaging to use to fill the prescription drug associated with the received request. In some embodiment, the determination of the packaging may be in response to receipt of the request for the prescription drug.

In some embodiments, the packaging determination made by the packaging determination module 408 is based on whether a blister packaging criterion has been met. The blister packaging criterion may identify a single prescription drug or multiple prescription drugs for blister packaging and reflect that a member or patient has had a prescription drug of the same or similar type that has previously been filled. For example, this determination may be on the basis of the patient (e.g., low patient adherence), on the basis of the prescription drug (e.g., commonly available and in a form that can be filled in blister packaging or is available in blister packaging), and the like. By making the determination, the packaging determination module 408 may identify the prescription drug associated with the current request to be filled with blister packaging.

By way of example, the prescription drug may be selected by the packaging determination module 408 among the prescription drugs that have previously been filled on behalf of the member to fill in blister packaging on behalf of the member. A determination may then be made by the packaging determination module 408 that the blister packaging criterion has been met based on selection of the prescription drug to fill in the blister packaging and receipt of the request for the prescription drug.

In some embodiments, the transmission module 410 transmits a blister fill instruction based on receipt of the request and a determination that the blister packaging criterion has been met. The blister fill instruction may reflect that the pharmacy device 102 is to fill the prescription drug utilizing blister packaging. In some embodiments, an adjudication response includes a blister fill instruction. In other embodiments, the blister fill instruction is sent separate from the adjudication response.

As described above, adherence may be determined by the adherence module 412 to determine whether a member should receive blister packaging. However, in some embodiments the adherence module 412 may determine adherence before and after a prescription drug is provided in blister packaging to determine a difference in adherence for the prescription drug provided in blister packaging and other prescription drugs that have not been provided to the member in blister packaging. Thus, the adherence module 412 may operate in conjunction with the analysis module 402 and/or the criterion selection module 410 to determine whether the member should receive the prescription drug in blister packaging as opposed to a fill in a prescription bottle.

By way of example, the adherence module 412 measures prior prescription drug adherence of the member prior to transmission of an adjudication response and measures after prescription drug adherence of the member for a period of time after transmission of the blister fill instruction, the period of time including at least one time period during which the prescription drug was prescribed to be taken by the member prior to prescription drug refill, and compares the prior prescription drug adherence and the after prescription drug adherence. The notification module 414 generates a notification based on comparison of the prior prescription drug adherence and the after prescription drug adherence. In some embodiments, the notification reflects that the after prescription drug adherence of the member is greater than the prior prescription drug adherence for both the prescription drug in blister packaging and any other drugs prescribed to be taken by the member that are not in blister packaging. As a result of the difference in adherence, the benefit manager, or another party, may receive a greater amount of reimbursement directly or indirectly from the client.

Not every prescription drug prescribed to the patient may be packaged in blister packaging. In some embodiments, the request receiver module 406 receives an additional request for an additional prescription drug prescribed for the member and the packaging determination module 408 determines that the blister packaging criterion has not been met based on a drug type of the prescription drug. As such, the packager of the prescription drugs (or the client, benefit manager, etc.) may not incur increased packaging cost for every prescription drug, but merely a subset of one or more than one prescription drug fulfilled for the member. The transmission module 410 may therefore transmits an additional response to the additional request. In some embodiments, the additional request reflects that the pharmacy is to fill the prescription drug accordance to standard fulfillment instructions.

The dispensing and packaging module 416 dispenses and packs a prescription drug into packaging (e.g., the prescription container). In some embodiments, the dispensing and packaging module 416 dispenses and packs the prescription drug into blister packaging based on receipt of the request for the prescription drug and a determination that the blister packaging criterion has been met. In some embodiments, the dispensing and packaging module 416 dispenses and packs the prescription drug into based on receipt of the blister fill instruction. The blister packaging may be performed by the pharmacy device 102 (e.g., at or before the time of fill), by a drug manufacture of the prescription drug, or otherwise. Once packed, the prescription drug may be provided to the member through mail order, in person (e.g., at a retail pharmacy), or otherwise.

Figure 5:
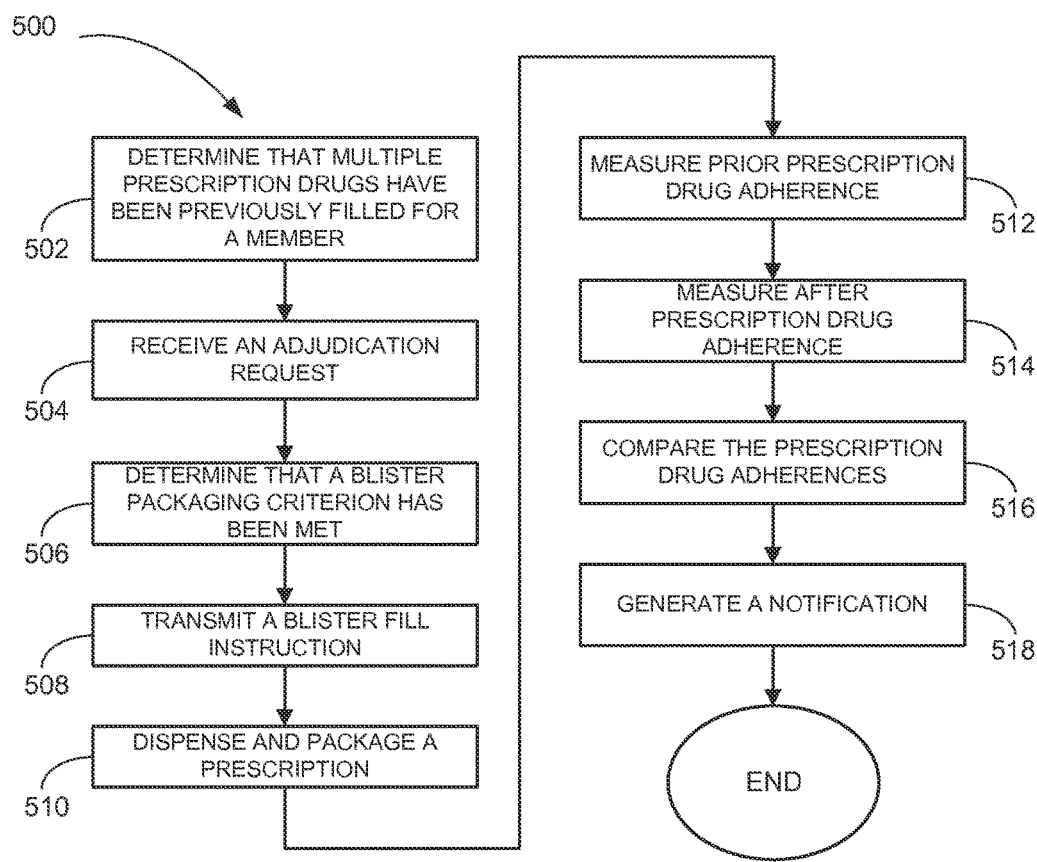
FIG. 5 is a block diagram of a flowchart illustrating a method for prescription drug packaging, according to an example embodiment.

FIG. 5 illustrates a method 500 for prescription drug packaging, according to an example embodiment. The method 500 may be performed by the pharmacy device 102, the benefit manager device 106, the member device 108, partially by the pharmacy device 102, the benefit manager device 106, the member device 108, partially by one, or more than one, of the foregoing devices 102, 106, 108, or may be otherwise performed.

At block 502, a determination that a member of a pharmacy benefit plan has had a multiple prescription drugs that have previously been filled is made. An adjudication request for a prescription drug prescribed for the member is received at block 504. The adjudication request may be based on a fulfillment request to fill the prescription drug.

A determination that a blister packaging criterion has been met is made at block 506 based on a drug type of the prescription drug and a determination that the member has had the prescription drugs that have previously been filled.

In some embodiments, the prescription drug is selected among the prescription drugs that have previously been filled on behalf of the member to fill in the blister packaging on behalf of the member. A determination that the blister packaging criterion has been met based is based on selection of the prescription drug to fill in the blister packaging and receipt of the adjudication request for the prescription drug.

A blister fill instruction is transmitted at block 508 based on receipt of the adjudication request and a determination that the blister packaging criterion has been met. The blister fill instruction may reflect that a pharmacy or pharmacy device 102 is to fill the prescription drug utilizing blister packaging.

At block 510, a prescription drug may be dispenses and packaged in blister packaging. The dispensing and packaging may be based on receipt of the blister fill instruction, based on receipt of the adjudication request and a determination that the blister packaging criterion has been met, or otherwise.

Prior prescription drug adherence of the member may be measured at block 512 prior to transmission of the adjudication response. At block 514, after prescription drug adherence of the member for a period of time may be measured after transmission of the blister fill instruction. The period of time may include one or more than one time period during which the prescription drug was prescribed to be taken by the member prior to prescription drug refill.

The prior prescription drug adherence and the after prescription drug adherence may be compared at block 516.

A notification may be generated at block 518 based on comparison of the prior prescription drug adherence and the after prescription drug adherence. The notification may reflect the difference in adherence based on the comparison.

In some embodiments, additional adjudication requests may be received for others prescription drugs prescribed for the member. When a determination is made for these drugs that the blister packaging criterion has not been met based on a drug type of the prescription drug, the member may be provided with standard packaging for the prescription drug. In some embodiments, an additional adjudication response to the additional adjudication request is transmitted reflecting that the pharmacy is to fill the prescription drug accordance to standard fulfillment instructions.

Figure 6:
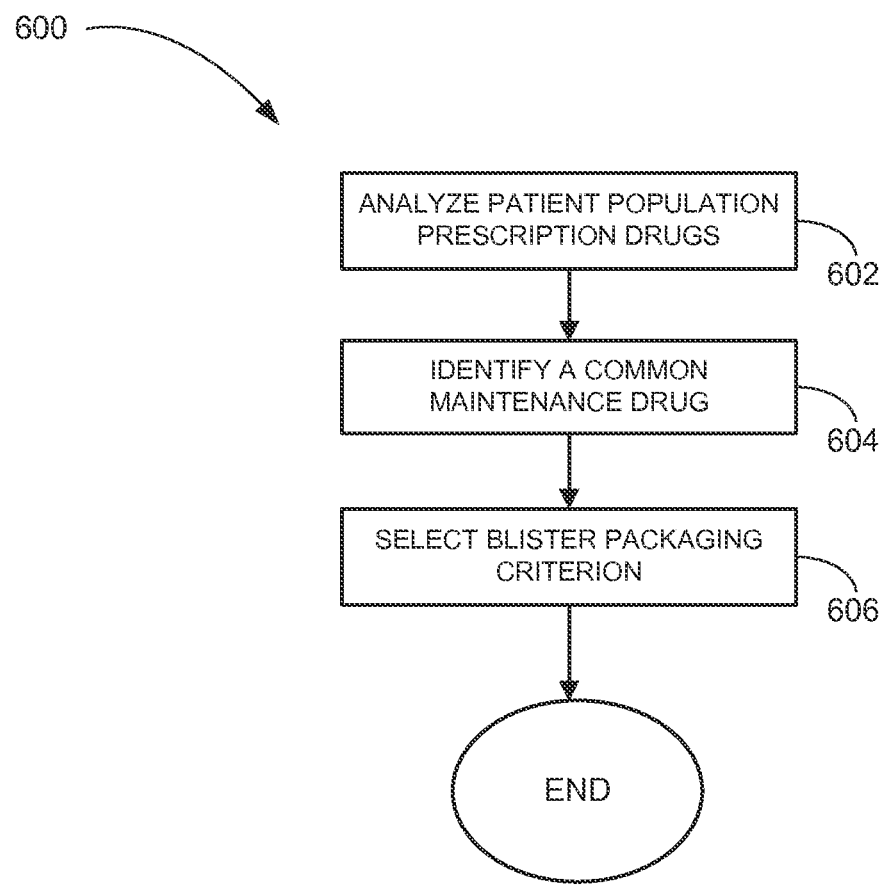
FIG. 6 is a block diagram of a flowchart illustrating a method for criterion selection, according to an example embodiment.

FIG. 6 illustrates a method 600 for criterion selection, according to an example embodiment. The method 600 may be performed by the pharmacy device 102, the benefit manager device 106, the member device 108, partially by the pharmacy device 102, the benefit manager device 106, the member device 108, partially by one, or more than one, of the foregoing devices 102, 106, 108, or may be otherwise performed.

Patient population prescription drugs that have been prescribed to a patient population are analyzed at block 602.

At block 604, the prescription drug is identified among the patient population prescription drugs as being a common maintenance drug that could be fulfilled through prescription bottle fulfillment or blister packaging fulfillment.

The blister packaging criterion is selected at block 606 based on identification of the prescription drug as being a common maintenance drug that could be fulfilled through prescription bottle fulfillment or blister packaging fulfillment.

While the foregoing methods and systems reflect that the packaging determination is made in response to an adjudication request, the packaging determination could be otherwise made. For example, some or all packaging determinations could be made in advance of adjudication requests so that when fill requests are received the appropriate drug packaging may already be available for fulfillment. As such, individualized notices of particular packaging may then not be sent.

Figure 7:
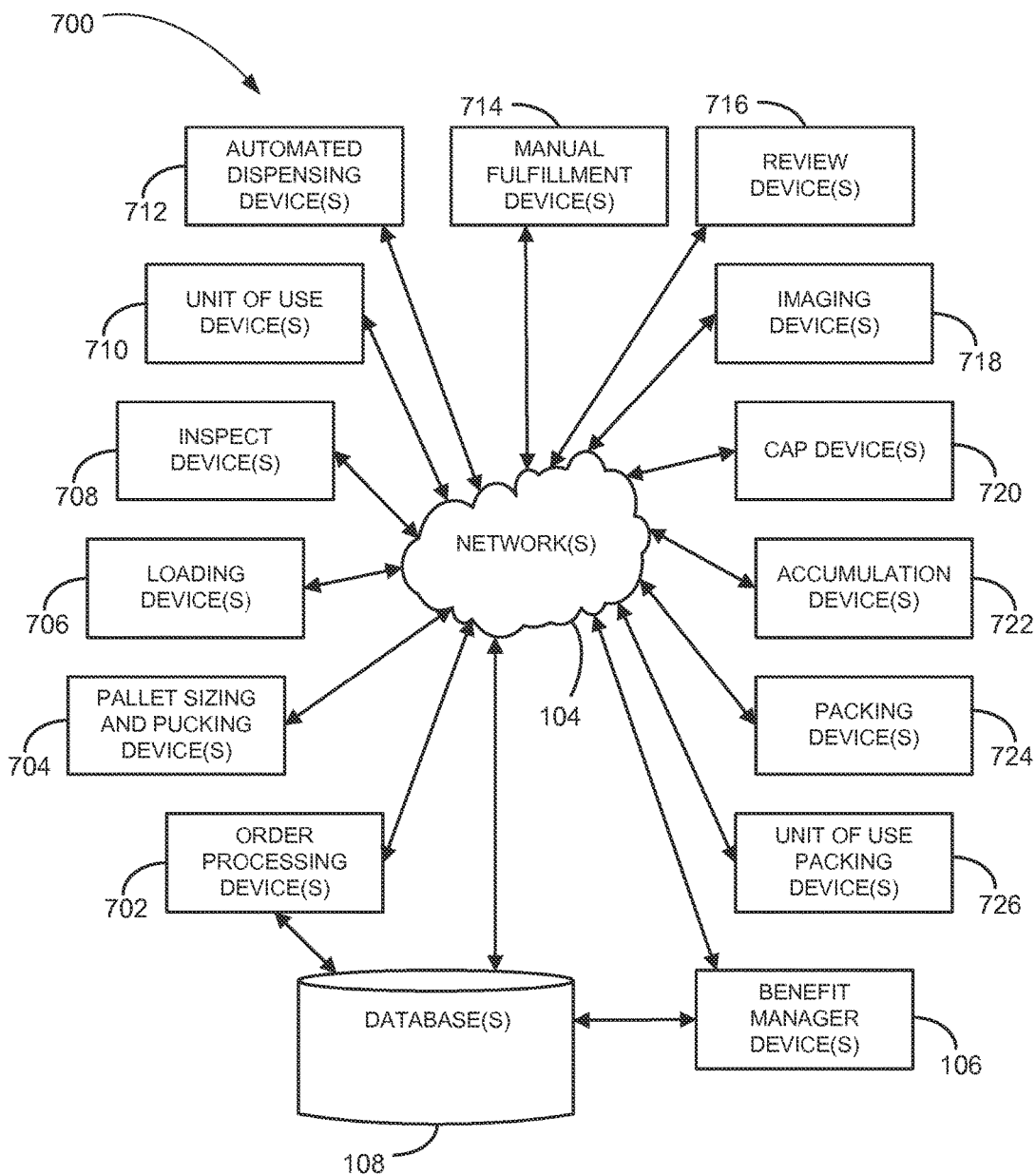
FIG. 7 is a block diagram of an example system according to an example embodiment.

FIG. 7 is a block diagram of an example system 700, according to an example embodiment. While the system 100 is generally described as being deployed in a high volume pharmacy (e.g., a mail order pharmacy, a direct delivery pharmacy, and the like), the system 100 may otherwise be deployed. In some embodiments, the system 100 includes the system 700. The pharmacy device 102 of FIG. 1 is reflected as devices 702-726 in the system 700.

The system 100 may include an order processing device 702 in communication with the benefit manager device 106 over the network 104. The order processing device 702 may receive information about prescriptions being filled at a pharmacy in which the order processing device 702 is deployed. The order processing device 702 may track a prescription order as it is fulfilled. A prescription order may include one or more than one prescription to be filled by the pharmacy. The order processing device 702 may make pharmacy routing decisions and/or order consolidation decisions for a prescription order. The pharmacy routing decisions include what device or devices in the pharmacy are responsible for filling at least a portion of the prescription order, where the order consolidation decisions include whether portions of a prescription order or multiple prescription orders should be shipped together for a patient or a patient family. The order processing device 702 may operate in combination with the benefit manager device 106.

In some embodiments, the order processing device 702 includes the packaging subsystem 202 and one or more than one of the modules 402-416.

The order processing device 702 and/or the benefit manager device 106 may be in communication directly (e.g., through local storage) and/or through the network 104 (e.g., in a cloud configuration or software as a service) with a database 108 (e.g., as may be retained in memory or otherwise). The database 108 may store order data, the member data 114, the claims data 116, the drug data 118, prescription data, and/or plan sponsor data. Other data may be stored in the database 108.

The order data may include data related to the order of prescriptions including the type (e.g., drug name and strength) and quantity of each prescription in a prescription order. The order data may also include data used for completion of the prescription, such as prescription materials. In general, prescription materials are a type of order materials that include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like.

The prescription data may include information regarding prescriptions that may be issued by prescribers on behalf of patients, who may be members of the drug benefit plan, for example to be filled by a pharmacy. Examples of the prescription data include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

The system 700 may include a pallet sizing and pucking device 704, a loading device 706, an inspect device 708, a unit of use device 710, an automated dispensing device 712, a manual fulfillment device 714, a review device 716, an imaging device 718, a cap device 720, an accumulation device 722, a packing device 724, and/or a unit of use packing device 726. The system 700 may also include additional devices. Order processing device 702 may direct at least some of the operations of these devices 704-726. In some embodiments, operations performed by one of these devices 704-726 may be performed sequentially, or in parallel with the operations of another device as may be coordinated by the order processing device 702.

In some embodiments, the system 700 may transport prescription drug containers by use of pallets. The pallet sizing and pucking device 704 may configure pucks in a pallet. A pallet may be a transport structure for a number of prescription containers, and may include a number of cavities. A puck may be placed in one or more than one of the cavities in a pallet by the pallet sizing and pucking device 704. A puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 702 based on prescriptions which the order processing device 702 decides to launch. In general, prescription orders in the database 108 reside in one or more than one queues, and are generally launched in a first-in-first-out order. However, the order processing device 702 may use logic and a variety of factors to determine when and how prescriptions are to be launched. For example, some non-limiting factors which may alter the first-in-first-out order of launching prescriptions in a pharmacy include the age of the order, whether the order required an outreach to a physician or some other intervention, whether there are any performance guarantees with plan sponsors or members, the available inventory of a given pharmaceutical in view of existing prescriptions already launched which will require that pharmaceutical, the zip code to which the order will be shipped, the workload and volume of various parts of the pharmacy, whether valid paperwork for the order has been received, and/or similar orders for the same pharmaceutical that are already to be launched. The logic may be implanted directly in the pallet sizing and pucking device 704, in the order processing device 702, in both devices 702, 704, or otherwise. Once a prescription is set to be launched, a puck suitable for the appropriate size of container for that prescription may be positioned in a pallet by a robotic arm or pickers. The pallet sizing and pucking device 704 may launch a pallet once pucks have been configured in the pallet.

The loading device 706 may load prescription containers into the pucks on a pallet by a robotic arm, pick and place mechanism, or the like. In one embodiment, the loading device 706 has robotic arms or pickers to grasp a prescription container and move it to and from a pallet. The loading device 706 may also print a label which is appropriate for a container that is to be loaded onto the pallet, and apply the label to the container. The pallet may be located on a conveyor assembly during these operations.

The inspect device 708 may verify that containers in a pallet are correctly labeled and in the correct spot on the pallet. The inspect device 708 may scan the label on one or more than one container on the pallet. Labels of containers may be scanned or imaged in full or in part. Such imaging may occur after the container has been lifted out of its puck by a robotic arm, picker, or the like, or may be otherwise scanned or imaged while retained in the puck.

The unit of use device 710 may temporarily store, monitor, label and/or dispense unit of use products. In general, unit of use products are prescription drug products that may be delivered to a patient or member without being repackaged at the pharmacy. These products may include pills in a container, pills in a blister pack, inhalers, and the like.

The automated dispensing device 712 may include one or more than one devices that dispense prescription drugs or pharmaceuticals into prescription containers such as prescription bottles and blister packs in accordance with one or multiple prescription orders. In general, the automated dispensing device 712 may include mechanical and electronic components with, in some embodiments, software and/or logic to facilitate pharmaceutical dispensing that would otherwise be performed in a manual fashion by a pharmacist and/or pharmacist technician. For example, the automated dispensing device 712 may include blister pack machines that dispense and pack drugs into a blister pack and/or a pill dispensing machines that that dispense and pack drugs into a prescription bottle.

The manual fulfillment device 714 may provide for manual fulfillment of prescriptions. For example, the manual fulfillment device 714 may receive or obtain a container and enable fulfillment of the container by a pharmacist or pharmacy technician. In some embodiments, the manual fulfillment device 714 provides the filled container to another device in the system 700 to be joined with other containers in a prescription order for a patient or member. In general, a manual fulfillment may include operations at least partially performed by a pharmacist or pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter).

The review device 716 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 716 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like.

The imaging device 718 may image containers once they have been filled with pharmaceuticals. The imaging device 718 may measure the fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon.

The cap device 720 may be used to cap certain types of prescription containers such as a prescription bottle. In some embodiments, the cap device 720 may provide a type of cap in accordance with a patient preference (e.g., a preference regarding child resistance), a plan sponsor preference, a prescriber preference, or the like. The cap device 720 may also etch a message into the cap, although this process may be performed by a subsequent device.

The accumulation device 722 accumulates various containers of prescription drugs in a prescription order. The accumulation device 722 may accumulate prescription containers from various areas of the pharmacy. For example, the accumulation device 722 may accumulate prescription containers from the unit of use device 710, the automated dispensing device 712, the manual fulfillment device 714, and the review device 716.

The packing device 724 packages a prescription order in preparation for shipping the order. The packed prescription order may package prescription containers that are of the same dimensions or different (e.g., different prescription bottle sizes, blister packaging and prescription bottle, and the like). The packing device 724 may box or bag the fulfilled prescription order for delivery. The packing device 724 may further place inserts into the box or bag. For example, bulk prescription orders may be shipped in a box, while other prescription orders may be shipped in a bag which may be a wrap seal bag. The packing device 724 may label the box or bag with the address and a recipient's name. The packing device 724 may sort the box or bag for mailing in an efficient manner (e.g., sort by delivery address). The packing device 724 may include ice or temperature sensitive processing for prescriptions which are to be kept within a temperature range during shipping in order to retain efficacy or otherwise. The ultimate package may then be shipped through postal mail, through a mail order delivery service that ships via group and/or air (e.g., UPS, FedEx, or DHL), through delivery service, through a locker box at a shipping site (e.g., Amazon locker or a PO Box), or otherwise.

The unit of use packing device 726 packages a unit of use prescription order in preparation for shipping the order. The unit of use packing device 726 may include manual scanning of containers to be bagged for shipping to verify each container in the order.

While the system 700 in FIG. 7 is shown to include single devices 106, 702-726 multiple devices may be used. The devices 106, 702-726 may be the same type or model of device or may be different device types or models. When multiple devices are present, the multiple devices may be of the same device type or models or may be a different device type or model. Moreover, the system 100 shows a single network 104; however, multiple networks can be used. The multiple networks may communicate in series with each other to link the devices 106, 702-726 or in parallel to link the devices 106, 702-726. Multiple devices may share processing and/or memory resources. The devices 106, 702-726 may be located in the same area or in different locations. For example, the devices 106, 702-726 may be located in a building or set of adjoining buildings. The devices 106, 702-726 may be interconnected (e.g. by conveyors), networked, and/or otherwise in contact with one another or integrated with one another. In addition, the functionality of a device may be split among a number of discrete devices and/or combined with other devices.

Multiple different configurations of the incorporation of the system 700 into the system 100 including the packaging subsystem 202 may be made. By way of example, the benefit manager device 106 may include the packaging subsystem 202 with the analysis module 402 and the criterion selection module 404, the order processing device 702 may include the packaging subsystem 202 with the request receiver module 406, the packaging determination module 408, and the transmission module 410, and the automated dispensing device 712 and/or the manual fulfillment device 714 may include the packaging subsystem 202 with the dispensing and packaging module 416. Other configurations may also be made.

Figure 8:
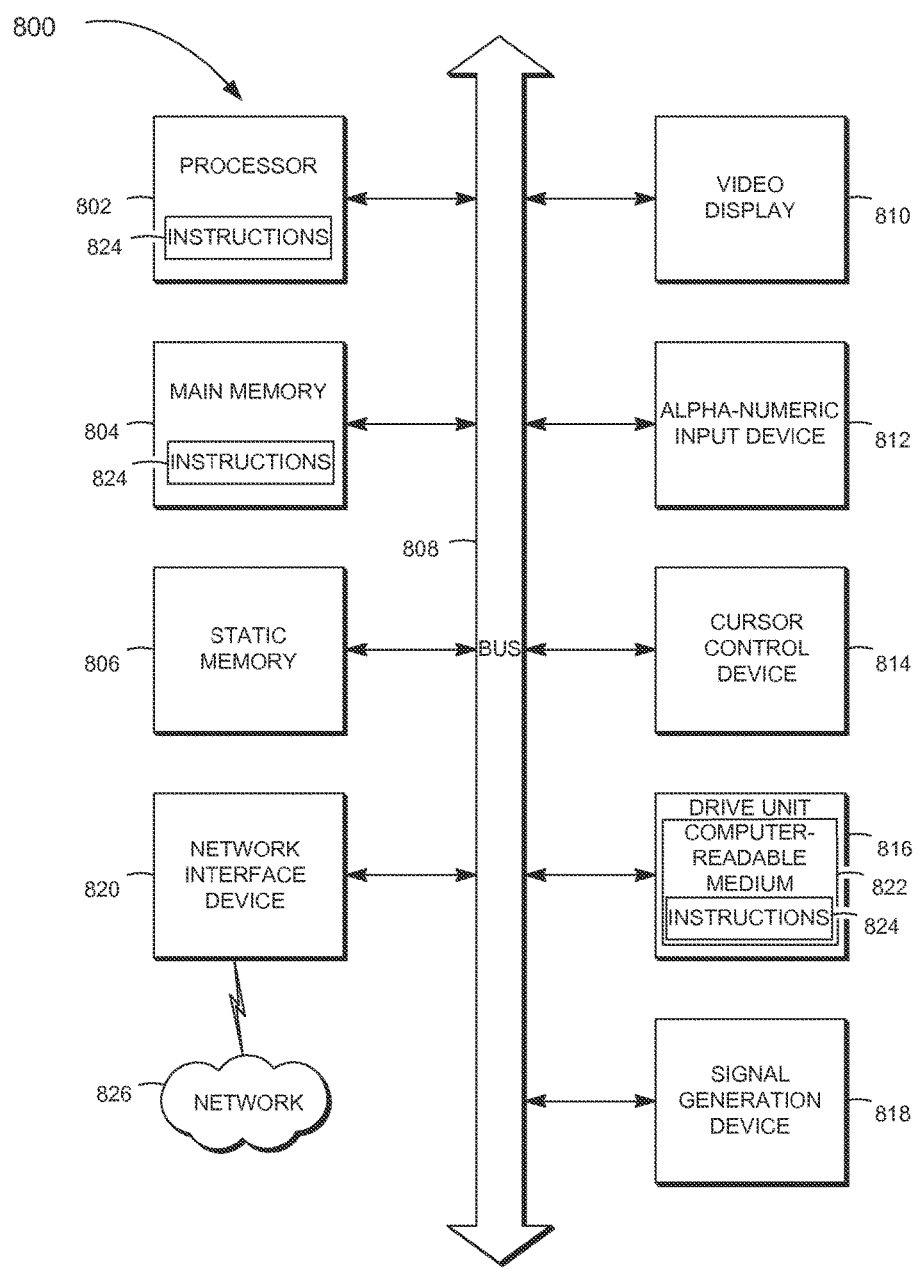
FIG. 8 is a block diagram of a machine in the example form of a computer system within which a set of instructions for causing the machine to perform any one or more of the methodologies discussed herein may be executed or stored.

FIG. 8 shows a block diagram of a machine in the example form of a computer system 800 within which a set of instructions may be executed causing the machine to perform any one or more of the methods, processes, operations, or methodologies discussed herein. The pharmacy device 102, the benefit manager device 106, the member device 108, and/or one or more of the devices 702-726 may include the functionality of the one or more computer systems 800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 800 includes a processor 812 (e.g., a central processing unit (CPU) a graphics processing unit (GPU) or both), a main memory 804 and a static memory 806, which communicate with each other via a bus 808. The computer system 800 further includes a video display unit 810 (e.g., a liquid crystal display (LCD) or a cathode ray tube (CRT)). The computer system 800 also includes an alphanumeric input device 812 (e.g., a keyboard), a cursor control device 814 (e.g., a mouse), a drive unit 816, a signal generation device 818 (e.g., a speaker) and a network interface device 820.

The drive unit 816 includes a computer-readable medium 822 on which is stored one or more sets of instructions (e.g., software 824) embodying any one or more of the methodologies or functions described herein. The software 824 may also reside, completely or at least partially, within the main memory 804 and/or within the processor 812 during execution thereof by the computer system 800, the main memory 804 and the processor 812 also constituting computer-readable media.

The software 824 may further be transmitted or received over a network 826 via the network interface device 820.

While the computer-readable medium 822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a determination that a member of a pharmacy benefit plan has had a plurality of prescription drugs that have previously been filled is made. An adjudication request for a prescription drug prescribed for the member is received. The adjudication request is based on a fulfillment request to fill the prescription drug. A determination that a blister packaging criterion has been met may be made based on a drug type of the prescription drug and a determination that the member has had the plurality of prescription drugs that have previously been filled. A blister fill instruction is transmitted based on receipt of the adjudication request and a determination that the blister packaging criterion has been met, wherein the blister fill instruction reflects that a pharmacy is to fill the prescription drug utilizing blister packaging.

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. As used herein, "a" or "an" may reflect a single part or multiple parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

Thus, systems and methods for prescription drug packaging have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A method comprising:
receiving, on a processor, an adjudication request for a prescription drug prescribed for a member of a pharmacy benefit plan, the adjudication request based on a fulfillment request to refill the prescription drug;
determining, on the processor, that the member has an adherence to a prescription drug regimen for the prescription drug that is below a threshold;
identifying, on the processor, that the prescription drug qualifies as a maintenance drug because the member of the pharmacy benefit plan has previously refilled the prescription drug multiple times through the pharmacy benefit plan;
determining, on the processor, that a blister packaging criterion has been met based on a determination that the adherence to the prescription drug regimen for the prescription drug is below the threshold, an identification that the prescription drug qualifies as a maintenance drug that has been previously refilled multiple times through the pharmacy benefit plan, and in response to receiving the adjudication request;
automatically transmitting a blister fill instruction in response to a determination that the blister packaging criterion has been met, wherein the blister fill instruction reflects that a pharmacy is to refill the prescription drug utilizing blister packaging instead of standard prescription packaging; and
a blister packing machine dispensing and packaging the prescription drug in the blister packaging in response to receipt of the blister fill instruction.

2. The method of claim 1, further comprising:
selecting the prescription drug among a plurality of prescription drugs that have previously been filled on behalf of the member to refill in the blister packaging on behalf of the member;
wherein a determination that the blister packaging criterion has been met is based on selection of the prescription drug to refill in the blister packaging and receipt of the adjudication request for the prescription drug.

3. The method of claim 1, further comprising:
measuring prior prescription drug adherence of the member for a first period of time prior to transmitting of the adjudication request;
measuring after prescription drug adherence of the member for a second period of time after transmission of the blister fill instruction, the second period of time including at least one time period during which the prescription drug was prescribed to be taken by the member prior to prescription drug refill;
comparing the prior prescription drug adherence and the after prescription drug adherence; and
generating a notification based on comparison of the prior prescription drug adherence and the after prescription drug adherence.

4. The method of claim 3, wherein the notification reflects that the after prescription drug adherence of the member is greater than the prior prescription drug adherence.

5. The method of claim 1, further comprising:
receiving an additional adjudication request for an additional prescription drug prescribed for the member; and
determining that the blister packaging criterion has not been met based on a drug type of the additional prescription drug.

6. The method of claim 5, further comprising:
transmitting an additional adjudication response to the additional adjudication request, the additional adjudication response reflecting that the pharmacy is not to refill the additional prescription drug in the blister packaging.

7. The method of claim 1, wherein an adjudication response to the adjudication request includes the blister fill instruction.

8. A system comprising:
a processor configured to:
receive an adjudication request for a prescription drug prescribed for a member of a pharmacy benefit plan, the adjudication request based on a fulfillment request to refill the prescription drug;
determine that the member has an adherence to a prescription drug regimen for the prescription drug that is below a threshold;
identify that the prescription drug qualifies as a maintenance drug because the member of the pharmacy benefit plan has previously refilled the prescription drug multiple times through the pharmacy benefit plan;
determine that a blister packaging criterion has been met based on a determination that the adherence to the prescription drug regimen for the prescription drug is below the threshold, an identification that the prescription drug qualifies as a maintenance drug that has been previously refilled multiple times through the pharmacy benefit plan, and in response to receiving the adjudication request; and
automatically transmit a blister fill instruction in response to a determination that the blister packaging criterion has been met, wherein the blister fill instruction reflects that a pharmacy is to refill the prescription drug utilizing blister packaging instead of standard prescription packaging; and
a blister packing machine configured to dispense and package the prescription drug in blister packaging in response to the blister fill instruction.

9. A non-transitory machine-readable medium comprising instructions, which when executed by one or more processors, cause the one or more processors to perform the following operations:
receive an adjudication request for a prescription drug prescribed for a member of a pharmacy benefit plan, the adjudication request based on a fulfillment request to refill the prescription drug;
determine that the member has an adherence to a prescription drug regimen for the prescription drug that is below a threshold;
identify that the prescription drug qualifies as a maintenance drug because the member of the pharmacy benefit plan has previously refilled the prescription drug multiple times through the pharmacy benefit plan;
determine that a blister packaging criterion has been met based on a determination that the adherence to the prescription drug regimen for the prescription drug is below the threshold, an identification that the prescription drug qualifies as a maintenance drug that has been previously refilled multiple times through the pharmacy benefit plan, and in response to receiving the adjudication request; and
automatically transmit a blister fill instruction to a blister packing machine in response to a determination that the blister packaging criterion has been met, wherein the blister fill instruction reflects that a pharmacy is to refill the prescription drug utilizing blister packaging instead of standard prescription packaging,
wherein a blister packing machine dispenses and packages the prescription drug in the blister packaging in response to receipt of the blister fill instruction.

10. The method of claim 3, wherein the first period of time covers the multiple times that the prescription drug has been refilled and ends at a time corresponding to receiving the adjudication request.

11. The method of claim 1, wherein determining the adherence to the prescription drug regimen comprises analyzing the member's drug history.

12. The method of claim 1, wherein the processor determines that the adherence to the prescription drug regimen is below the threshold comprises the processor determining that the adherence to the prescription drug regimen is below the threshold for a time period that covers the multiple times that the prescription drug has been refilled and ends at a time corresponding to receiving the adjudication request.

* * * * *